United States Patent [19]

Askanazi et al.

[11] Patent Number: 5,064,810
[45] Date of Patent: Nov. 12, 1991

[54] USE OF BRANCHED CHAIN AMINO ACIDS TO EFFECT DIAPHRAGM CONTRACTILITY AND FATIGUE

[76] Inventors: Jeffrey Askanazi, 233 Myrtle St., Haworth, N.J. 07641; Susan Trimbo, 737 Ridge Ave., Evanston, Ill. 60202

[21] Appl. No.: 583,177

[22] Filed: Sep. 14, 1990

[51] Int. Cl.$^5$ .................. A61K 31/19; A61K 31/195; A61K 37/00
[52] U.S. Cl. ....................... 514/2; 514/557; 514/561
[58] Field of Search .................. 514/561, 557, 2

[56] References Cited

U.S. PATENT DOCUMENTS 4,687,782  8/1987  Brantman ..................... 514/561

OTHER PUBLICATIONS

*Chemical Abstracts*, 107(7):56571g (1987), Mohan et al., Fatigue Induced Alterations in Muscle Transamination Patterns of Albino Rat.
BIOSIS No. 83027653, (Abstract), 1986, Fielding et al., The Effects of High Intensity Exercise on Muscle and Plasma Levels of Alpha Ketoisocaproic-Acid.
B. Skeie et al., Branch-Chain Amino Acids: Their Metabolism and Clinical Utility, Critical Care Medicine, vol. 18, No. 5, May 1990, pp. 549-571.
A. Wagenmakers et al., The Metabolic Fate of Branched-Chain Amino Acids and 2-Oxo Acids in Rat Muscle Homogenates and Diaphragms, Int. J. Biochem., vol. 17, No. 9, 1985, pp. 957-965.
T. Normal Palmer et al., Modulation of Branched-Chain Amino Acid Oxidation in Rat Hemidiaphragms in Vitro by Glucose and Ketone Bodies, Biochemistry International, vol. 11, No. 3, Sep. 1985, pp. 407-413.
S. Weinberger, M.D. et al., Hypercapnia, The New England Journal of Medicine, vol. 321, No. 18, Nov. 2, 1989, pp. 1223-1231.

*Primary Examiner*—Stanley J. Friedman
*Attorney, Agent, or Firm*—Hill, Van Santen, Steadman & Simpson

[57] ABSTRACT

A method for reducing respiratory muscle fatigue comprising the steps of administering a composition that includes branched chain amino acids. The composition can be administered either enterally or parenterally.

17 Claims, No Drawings

USE OF BRANCHED CHAIN AMINO ACIDS TO EFFECT DIAPHRAGM CONTRACTILITY AND FATIGUE

BACKGROUND OF THE INVENTION

The present invention relates to the treatment of respiratory disorders. More specifically, the present invention relates to the treatment of poor respiratory muscle function.

Due to a number of disease states, and other disorders, many patients present poor respiratory muscle function. Respiratory-muscle fatigue can result in carbon dioxide retention in patients and can be the result of respiratory disease, malnutrition, neuromuscular disorder, or other abnormal states. Respiratory-muscle fatigue can result in hypercapnia and in ventilatory failure.

Fatigue of the diaphragm has been defined as an inability to continue generating a sufficient pressure to maintain adequate alveolar ventilation. The failure to maintain adequate ventilation results when the tension produced by the diaphragm consistently exceeds 40 percent of the maximal level. Additionally, fatigue of the respiratory muscles occurs when mouth pressure consistently exceeds 50 to 70 percent of maximal levels that can be generated. Roussos, C., Macklem, P.T., *The Respiratory Muscles*, New England Journal of Medicine 1982; 307: 786-97.

Respiratory-muscle fatigue is believed to develop when the energy requirements of the diaphragm muscles exceed the energy supply. Weinberger et al, *Hypercapnia*, The New England Journal of Medicine, 1989; 321: 1223-1231. A number of factors can increase energy demands, or decrease available energy, increasing the likelihood of muscle fatigue. For example, low cardiac output, anemia, and decreased oxygen saturation can result in decreased energy supply and therefore an increased likelihood of respiratory-muscle fatigue. With respect to an increase in energy demands, this can occur due to high levels of ventilation or an increase in the breathing effort, for example, increased resistance to air flow or decreased compliance of the respiratory system.

Additionally, factors that decrease muscle strength can also predispose a patient to respiratory muscle fatigue. Therefore, respiratory muscle fatigue can be associated with primary neuromuscular disease, malnutrition, or electrolyte alterations, for example, hypokalemia and hypophosphatemia can cause substantial weakness of the respiratory muscles and contribute to or precipitate hypercapnic ventilatory failure.

Pharmaceutical intervention to improve diaphragmatic function has been proposed. Theophylline and sympathomimetic agents have been suggested as theoretically improving diaphragmatic function; But, their clinical utility in this regard is controversial. Muxnam, *Aminophylline and the Respiratory Muscles: an Alternative View*, Clinical Chest Medicine 1988; 9:325-36. Diaphragmatic rest using a mechanical ventilatory support has been used in patients wherein respiratory muscle fatigue has contributed to hypercapnic respiratory fatigue. Peters, et al, *Home Mechanical Ventilation*, Mayo Clinic Procedure, 1988; 63:1208-13.

SUMMARY OF THE INVENTION

The present invention provides a therapy for patients with poor respiratory muscle function. To this end, the present invention provides a method for reducing diaphragm muscle fatigue and improving contractility comprising administering to a patient having poor respiratory muscle function a composition including branched chain amino acids.

In an embodiment, the composition is administered parenterally.

In a further embodiment, the composition is administered enterally.

In an embodiment, a method is provided for treating poor respiratory muscle function comprising administering to a patient having poor respiratory function, a composition including leucine.

In another embodiment, a method for treating poor respiratory function is provided comprising administering parenterally to a patient having poor respiratory function a branched chain amino acid solution comprising (per 100 ml): 1.38 g isoleucine; 1.38 g leucine; and 1.24 g valine.

In a further embodiment, a method for treating poor respiratory function is provided comprising administering enterally a composition including at least 1.38 g per 100 ml leucine.

In another embodiment, a method for treating poor respiratory function is provided comprising administering enterally to a patient having poor respiratory function a composition including at least leucine with or without other nutrients such as fats and carbohydrates. The enteral composition can also include isoleucine and valine.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a method for treating patients with poor respiratory muscle function and/or respiratory muscle fatigue. Specifically, the method comprises administering to a patient with a poor respiratory function a composition including branched chain amino acids (leucine, valine, and isoleucine). The composition can be administered either parenterally or enterally. The composition results in improved pulmonary function and can be used, for example, to accelerate the weaning of a patient from a mechanical ventilator.

It has also been found that leucine alone provides therapeutic results in treating patients with poor respiratory function and improves pulmonary function.

By way of example, an example of a formulation that can be administered parenterally is as follows: a branched chain amino acid solution comprising (per 100 ml): 1.38 g isoleucine; 1.38 g leucine; and 1.24 g valine.

A further example of a formulation that can be used for treating poor respiratory function comprises a composition including at least 1.38 g leucine per 100 ml.

In an embodiment, 4 grams of branched chain amino acids are administered, parenterally, per hour.

Of course, the branched chain amino acids can be administered with other nutrients and medicaments. For example, if administered enterally, the branched chain amino acids can be administered with fats, carbohydrates, and other nutrients.

It should also be noted that the branched chain amino acids can be administered in other forms, for example, as part of a protein or peptide.

By way of example, and not limitation, examples of the invention will now be given.

EXAMPLE 1

Branched chain amino acid and glucose were compared to determine the effect on contractility and fatigue of isolated rat hemidiaphragm. Two groups of Wistar rats were compared. The groups were equilibrated with either Krebs Ringer Buffer solution (KRB), which contains 200 mg/dl of glucose and a mixture of leucine, valine and isoleucine (BCAA, n=6), or a higher concentration of glucose (800 mg/dl, n=6). Each group was examined with paired controls (KRB, n=12).

Muscles were stimulated directly under complete neuromuscular block. Fatigue was induced by 10 minute stimulation with 30 trans/minutes of 5 Hz at a 50% duty cycle. Isometric tension elicited by single and tetanic (10 to 100 Hz) stimulation was measured at baseline, after 2 hours of equilibration (T2) and at 0, 10, 30, and 60 (T6) minutes after induction of fatigue.

The tension difference (% of baseline in treatment−% of baseline in paired controls) at T2 was $17\pm3$ and $13\pm5$ at single twitch, $19\pm5$ and $20\pm10$ at 10 Hz, $11\pm6$ and $21\pm8$ at 20 Hz, $9\pm4$ and $14\pm4$ at 60 Hz, and $8\pm3$ and $9\pm3$ at 100 Hz (mean$\pm$SE) in branched chain amino acids and glucose, respectively. All values were significantly higher ($p<0.05$) than paired controls.

After induction of fatigue, the recovery, at T6, was significantly ($p<0.05$) better with branched chain amino acid compared with control at all frequencies of stimulation. There was no significant difference between the control and glucose.

Contractility after equilibration with branched chain amino acids or with high concentration of glucose increased in a similar manner. But, branched chain amino acids not glucose significantly improved recovery from fatigue. Accordingly, branched chain amino acids improve the recovery from fatigue that was induced by direct stimulation of isolated rat hemidiaphragm.

EXAMPLE 2

The contribution of individual amino acids to the recovery of fatigue was studied.

Five groups of Wistar rats isolated hemidiaphragms were equilibrated with Krebs Ringer Buffer solution (KRB) alone (as paired controls, n=24), or with Krebs Ringer buffer plus leucine (n=6), valine (n=6), isoleucine (n=6), or all three (BCAA, n=6).

The hemidiaphragms were then stimulated directly under complete neuromuscular block. Fatigue was induced by 10 minutes of stimulation with 30 trains/min of 5 Hz at a 50% duty cycle. Isometric tensions elicited by single and tetanic (10 to 100 Hz) stimulation were measured at baseline, after 2 hours of equilibration, and at 0, 10, 30, and 60 minutes (T6) after induction of fatigue.

The percent of baseline at T6 elicited by stimulation at 100 Hz (mean$\pm$SE) was $58\pm5$, $78\pm2$ ($p<0.01$), $76\pm2$ ($p<0.01$), $70\pm5$ (ns), and $64\pm5$ (ns) for Krebs Ringer buffer, branched chain amino acids, leucine, valine, and isoleucine, respectively. The tension difference (% of baseline in treatment−% of baseline in paired control), at T6, from stimulation at 100 Hz was $23\pm5\%$ with branched chain amino acids and $21\pm4\%$ with leucine.

The experiment suggests that a substantial portion of the effect of branched chain amino acids on reduction of fatigue in isolated rat hemidiaphragm is mediated by leucine.

EXAMPLE 3

The effect of branched chain amino acids and AMP on contractility and fatigue of isolated rat hemidiaphragm was studied. Two groups of Wistar isolated rat hemidiaphragm were equilibrated with Krebs Ringer Buffer solution (KRB) and either a mixture of leucine, valine, and isoleucine (branched chain amino acids, n=6), or 500 $\mu$g/ml of AMP (n=6). Each group was examined with paired controls (KRB, n=12).

Muscles were stimulated directly under complete neuromuscular block. Fatigue was induced by 10 minutes of stimulation with 30 trains/min of 5 Hz at 50% duty cycle. Isometric tension elicited by single and tetanic (10 to 100 Hz) stimulation was measured at baseline, after 2 hours of equilibration (T2), and at 0, 10, 30, and 60 (T6) minutes after induction of fatigue.

Tension differences (% of baseline in treatment of−% of baseline in control) at T2 were $60\pm5$ ($p<0.01$) at single twitch, $42\pm5$ ($p<0.01$) at 10 Hz, $27\pm5$ ($p<0.01$) at 20 Hz, $6\pm3$ (ns) at 60 Hz and $-4\pm5$ (ns) at 100 Hz (mean$\pm$SE) in AMP. In branched chain amino acids, tension differences at T2 were $22\pm3$, $19\pm5$, $11\pm6$, $9\pm4$, and $8\pm3$, respectively, ($p<0.05$) at all frequencies. At T6 in AMP, tensions were higher than control ($p<0.01$) at single twitch and 10 Hz, but lower ($p<0.01$) at 100 Hz. In branched chain amino acids, tensions were higher ($p<0.05$) than control at each frequency of stimulation.

The experiment and data suggest that branched chain amino acids improve contractility and fatigue at all frequencies. AMP improves contractility and fatigue at low frequencies but adversely affects recovery from fatigue at high frequencies.

EXAMPLE 4

This contemplated example illustrates the use of the method of the present invention for treating diaphragm fatigue.

A sixty four year old male underwent a coronary bypass procedure. Post-surgery the patient was placed on mechanical ventilation.

A 5% dextrose solution was administered on Day 1 post-op. On Day 3 the patient was given parenterally an 85% branched chain amino acid (BCAA) solution (4% BranchAmin). Pulmonary function was assessed at Day 1 and Day 4, parameters relevant to diaphragm function are set forth below:

|  | DAY 1 DEXTROSE | DAY 4 BCAA |
|---|---|---|
| $PaCO_2$ (kPa) | 5.75 | 4.97 |
| Vd/Vt (%) | 38 | 48 |
| $VCO_2$ (ml/kg) | 2.9 | 3.0 |
| VA (ml/kg) | 65 | 60 |
| Inspiratory flow (cm $H_2O$) |  | −20 |
| Expiratory flow (cm $H_2O$) |  | +40 |

Pulmonary function improved sufficiently to warrant early weaning from mechanical ventilation on Day 8.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for reducing diaphragm muscle fatigue and improving contractility comprising administering to a patient having poor respiratory muscle function a composition comprising at least the branched chain amino acids, leucine, valine and isoleucine in amounts effective to reduce diaphragm muscle fatigue including branched chain amino acids.

2. The method of claim 1 wherein the composition is administered parenterally.

3. The method of claim 1 wherein the composition is administered enterally.

4. The method of claim 1 wherein the composition includes peptides that provide the branched chain amino acids.

5. The method of claim 1 wherein the composition includes at least approximately 1.38 gms of leucine per 100 ml of composition.

6. The method of claim 2 wherein approximately 4 grams of branched chain amino acids are administered per hour.

7. A method for treating poor respiratory muscle function comprising administering to a patient having poor respiratory function a composition comprising at least the branched chain amino acids, leucine, valine and isoleucine in amounts effective to reduce diaphragm muscle fatigue comprising leucine.

8. The method of claim 7 wherein the composition is administered parenterally.

9. The method of claim 7 wherein the composition is administered enterally.

10. The method of claim 7 wherein at least 1.38 gms of leucine are included in the composition per 100 ml.

11. The method of claim 7 wherein the composition comprising peptides that provide the leucine.

12. A method for treating poor respiratory muscle function comprising administering to a patient having poor respiratory function a composition that provides to the patient at least approximately 1.38 gms of leucine per 100 ml of composition administered.

13. The method of claim 12 wherein the composition is administered parenterally.

14. The method of claim 12 wherein the composition also provides at least approximately 1.38 g of isoleucine and 1.24 g of valine per 100 ml.

15. The method of claim 12 wherein the composition comprising peptides that provide leucine.

16. The method of claim 15 wherein the composition includes peptides that provide isoleucine and valine.

17. The method of claim 1 wherein the composition includes other nutrients.

* * * * *